United States Patent [19]

Xu et al.

[11] Patent Number: 5,861,445

[45] Date of Patent: Jan. 19, 1999

[54] REINFORCEMENT OF DENTAL AND OTHER COMPOSITE MATERIALS

[75] Inventors: Huakun Xu, Gathersburg; Frederick C. Eichmiller, Ijamsville, both of Md.

[73] Assignee: American Dental Association Health Foundation, Gaithersburg, Md.

[21] Appl. No.: 852,900

[22] Filed: May 8, 1997

[51] Int. Cl.$^6$ .................................. C08K 9/00; C08K 3/40
[52] U.S. Cl. .......................... 523/116; 523/216; 523/217; 523/115; 523/117; 524/443; 524/450; 524/494; 524/790; 524/791; 106/35; 433/228.1; 501/35; 501/134; 501/151; 65/117
[58] Field of Search ................................... 523/116, 217, 523/216, 117; 524/443, 450, 494, 790, 791; 106/35; 433/228.1; 501/35, 134, 151; 65/117

[56] References Cited

U.S. PATENT DOCUMENTS

| | | | |
|---|---|---|---|
| 4,107,845 | 8/1978 | Lee, Jr. et al. | 523/116 |
| 4,463,058 | 7/1984 | Hood et al. | |
| 4,527,979 | 7/1985 | McLean et al. | |
| 4,548,774 | 10/1985 | Aklyama et al. | |
| 4,613,646 | 9/1986 | Robeson et al. | |
| 4,687,205 | 8/1987 | Tominaga et al. | |
| 4,816,495 | 3/1989 | Blackwell et al. | |
| 5,078,596 | 1/1992 | Carberry et al. | |
| 5,130,347 | 7/1992 | Mitra | |
| 5,154,762 | 10/1992 | Mitra et al. | |
| 5,166,004 | 11/1992 | Bose et al. | |
| 5,171,489 | 12/1992 | Hirao et al. | |
| 5,187,021 | 2/1993 | Vyrdra et al. | |
| 5,189,077 | 2/1993 | Kerby | |
| 5,228,907 | 7/1993 | Eppinger et al. | 523/115 |
| 5,367,002 | 11/1994 | Huang et al. | |
| 5,407,754 | 4/1995 | Harada et al. | |
| 5,453,456 | 9/1995 | Mitra et al. | 523/116 |
| 5,464,583 | 11/1995 | Leesing | |
| 5,525,148 | 6/1996 | Chow et al. | |
| 5,621,035 | 4/1997 | Lyles et al. | 523/116 |
| 5,707,734 | 1/1998 | Hawkins et al. | 523/217 |

FOREIGN PATENT DOCUMENTS

| | | | |
|---|---|---|---|
| 2028855 | 3/1990 | United Kingdom | 523/116 |

OTHER PUBLICATIONS

Mazer et al., –"Evaluating A Microfill Posterior Composite Resis (A Five–Year Study)" –JADA, vol. 123, pp. 33–38 (Apr. 1992).
Bayne et al. –"Update On Dental Composite Restorations" –JADA, vol. 125, pp. 687–701 (Jun. 1994).
Leinfelder –"Posterior Composite Resins" –JADA, vol. 126, pp. 663–676 (May 1996).
Willems et al. –"A Classification of Dental Composite According To Their Morphological and Mechanical Characteristics" –Dental Materials, pp. 310–319 (Sep. 1992).
Ferracane et al., –"Properties of Posterior Composite –Results of Round Robin Testing for a Specification" –Dental Materials, pp. 92–99 (Mar. 1994).
Goldberg et al. –"Screening of Matrices and Fibers for Reinforced Thermoplastics Intended for Dental Applications" –Journal of Biomedical Materials Research, vol. 28, pp. 167–173 (1994).
Goldberg et al. –"The Use of Continuous Fiber Reinforcement in Dentistry" –Dental Materials, pp. 197–202 (May 1992).
Henry et al. –"Fiber–Reinforced Plastics for Interim Restorations" –QDT, pp. 110–123 (1990/91).
Becher et al. –"Toughening Behavior in SiC Whisker–Reinforced Alumina" –Communications of the American Ceramic Society, pp. C–267–C–269 (Dec. 1984).
Simmons –"Silver–Alloy Powder and Glass Ionomer Cement" –JADA, vol. 120, pp. 49–52 (Jan. 1990).
Mathis et al. –"Properties of a Glass–Ionomer/Resin–Composite Hybrid Material" –Dental Materials, pp. 355–358 (Sep. 1989).
Uno et al. –"Long–Term Mechanical Characteristics of Resin–Modified Glass Ionomer Restorativo Materials" –Dental Materials, pp. 64–69 (Jan. 1996).
McLean et al. –"Cermet Cements"–JADA, vol. 120, pp. 43–47 (Jan. 1990).
Prosser et al. –"Glass–Ionomer Cements of Improved Flexural Strength" –J. Dent. Res. pp. 146–148 (Feb. 1986).
Grant –"Whisker Reinforcement of Polymethyl Methacrylate Denture Base Resins" –Australian Dental Journal, pp. 29–33 (Feb. 1967).
Academy of Dental Materials –Proceedings of Conference on "Clinically Appropriate Alternatives to Amalgam: Biophysical Factors in Restorative Decision–Making", Oct. 30 –Nov. 2, 1996, vol. 9, 1996, pp. 238 and 273.

*Primary Examiner*—Andrew E. C. Merriam
*Attorney, Agent, or Firm*—Banner & Whitcoff Ltd.

[57] ABSTRACT

A composition useful as a restorative material includes a curable matrix with whiskers which preferably have a silicon dioxide containing coating thereon that are then silanized and may also include optional particulate filler of the type which may release fluorides. The polymeric matrix bonds more tightly to the whiskers due to the coating of silicon dioxide on the surface of the whiskers and the coaction between said silicon dioxide and the silane compound. Particles adhered to the whisker also enhance the mechanical properties by virtue of the whisker's surface being thereby roughened. A method of manufacture is also disclosed.

33 Claims, 3 Drawing Sheets

REINFORCEMENT OF DENTAL AND OTHER COMPOSITE MATERIALS

This invention was made in the course of research partially supported by a grant from the National Institute of Dental Research (Grant No. P50DG09322). The U.S. government has certain rights in the invention.

BACKGROUND OF THE INVENTION

1. Field of the Invention

This invention relates to structurally unique polymeric composites, including composites with novel reinforcement systems. This invention further relates to new types of polymeric composites, compomers, resin-modified glass ionomers and glass ionomers that contain novel reinforcement systems as well as ion-releasing fluorosilicate glasses for fluoride release. More particularly, in its preferred embodiment, the invention relates to polymeric dental composites, compomers, resin-modified glass ionomers and glass ionomers containing elongated whisker fillers, including single-crystalline ceramic whiskers, polycrystalline chopped fibers, chopped glass fibers, and chopped polymer fibers. Further, this invention relates to methods and compositions for: (1) blending whiskers and/or chopped fibers with ground pre-cured glass ionomer cements in powder form, and/or ion-releasing fluorosilicate glass and polyacid for fluoride release; (2) mixing whiskers and/or chopped fibers with silicate particulate fillers for improved filler distribution in matrix, thereby minimizing whisker and/or chopped fiber entanglement; and (3) coating and bonding silicate filler particles and/or ion-releasing fluorosilicate glass particles onto the surfaces of individual whiskers or chopped fibers for ease of silanization and improved whisker retention in matrix by providing rougher particle-bonded whisker surfaces. The reinforced material systems are useful for the preparation of dental and medical adhesives, bases, liners, luting agents, sealants, core buildup and direct filling materials, inlays and onlays for restorative uses, as well as for endodontic and orthopedic use.

2. Description of the Prior Art

The dental composite resins can be viewed as one extreme of a continuous spectrum of multi-phase dental materials with the glass ionomers at the other extreme, and hybrid materials such as resin-modified glass ionomers and compomers intermediary in the spectrum. Whereas both composite resins and glass ionomers have been known and used for over two decades, the hybrid materials such as the resin-modified glass ionomers and compomers are relatively new and have only been available for about half a decade.

2.a Polymeric Composites

In the area of dental restorative materials, ceramic filler reinforced polymeric composites are widely used. A typical dental composite is composed of a mixture of silicate glass or quartz particles with an acrylic monomer that is polymerized to form a hardened composite material. In current dental composites, the fillers are mostly glasses, occasionally glass-ceramics and quartz (a crystalline form of silica), particulate polymers and glass-polymer composite particulates. Current strategies for their improvement include the development of smaller filler particles such as microfiller and nanofiller particles, the improvement of glass compositions, and the increase of filler volume fraction through the use of hybrid and heterogeneous filler systems.

Due to concerns about the release of mercury from dental amalgam, there is an increasing need to extend the use of polymeric composites to stress bearing posterior applications. However, the relatively low toughness, strength, wear resistance and durability of dental composites have limited their use. It is generally agreed that polymeric composites "cannot be routinely substituted for dental amalgam and achieve the same clinical results. In the posterior dentition, in situations where occlusal stresses are concentrated, the current composites . . . are inappropriate choices" (Corbin and Kohn, 1994, JADA 125: 381–388). The current polymeric composites "are not recommended for large posterior restorations because of the potential for excessive wear, microleakage or fracture" (Bayne et al. 1994, JADA 125: 687–701). Composite restorations, in low stress-bearing applications not involving cusps, have average lifetimes of less than 10 years. In comparison, dental amalgam restorations, in high stress-bearing posterior applications with cusp replacement, have lifetimes of 15 years (Corbin and Kohn, 1994, JADA 125: 381–388).

2.b Glass Ionomers, Resin-modified Glass Ionomers and Compomers

Radical changes have occurred during the past decade in dental restorative materials. However, none has had a greater impact than the fluoride-releasing glass ionomer materials. Glass ionomer materials are based on the acid-base reaction of an aqueous solution of a polycarboxylic acid with an ion leachable, fluoride-containing glass (Wilson and Kent, J Appl Chem Biotechnol 21: 313, 1971; Wilson and Kent, Br Dent J 132: 133, 1972; Wilson and Kent, Br Pat 1,316,129, 1973; Wilson and Crisp, Br Pat 1,422,337, 1976). Glass ionomers are noted for their inherent adhesiveness to teeth and their ability to release fluoride to adjacent tooth structure in a sustained fashion to combat secondary caries. However, the inferior mechanical properties of glass ionomers, especially their extreme brittleness and low strength (e.g., flexural strength of 10–20 MPa, McLean, J Am Dent Assoc 120: 43, 1990) have severely limited their use. The reinforcement of glass ionomers by disperse phase Corundum (Prosser et al., J Dent Res 65: 146, 1986), alumina fibers and other fibers (Sced and Wilson, Br Pat Appli GB 2,028,855A, 1978), and metal powders (McLean and Gasser, U.S. Pat. No. 4,527,979, 1985) resulted in only incremental improvement in mechanical properties. Flexural strength values of reinforced glass ionomers have rarely exceeded 50 MPa (Wilson and McLean, Glass-Ionomer Cement, 1988; McLean, J Am Dent Assoc 120: 43, 1990).

Resin-modified glass ionomers (Mitra, Eu Pat Appl 323120, 1988; U.S. Pat. No. 5,154,762, 1992), where compatible resins (e.g., 2-hydroxyethyl methacrylate, or HEMA) are used with the polyacids, are only slightly stronger than glass ionomers (e.g., flexural strength of 60 MPa, Poolthong et al., Dent Mater J 13: 220, 1994; Hickel, Acad Dent Mater Trans 9: 105, 1996). It is widely recognized that "the most intractable problem is likely to be lack of strength and toughness" (Wilson and McLean, Glass-Ionomer Cement, 1988).

Recently, a possible breakthrough occurred with the development of compomers (Blackwell et al., U.S. Pat. No. 4,816,495, 1989; Huang et al., U.S. Pat. No. 5,367,002, 1994; Peters et al., J Dent Res 73, 1994; Peters et al., J Dent Res 74, 1995; Barnes et al., J Dent Res 75: 293, 1996; Hickel, Acad Dent Mater Trans 9: 105, 1996; Blackwell et al., Acad Dent Mater Trans 9: 77, 1996). Compomers are basically hybrid, glass ionomer-composites modified in their resin phase by a carboxylic acid monomer and in their filler phase by the inclusion of an acid-reactive, ion-leachable glass. The name compomer is derived by combining the two words composite and ionomer, and is intended to suggest a combination of composite and glass-ionomer technology.

The liquid part of a compomer is a mixture of a dental resin monomer (such as UDMA, a urethane dimethacrylate) and a carboxylic acid monomer (e.g., TCB, the reaction product of butane tetracarboxylic acid with HEMA), with the resin being the major phase and TCB the minor phase. The filler part of a compomer is a mixture of dental silicate glass and reactive fluorosilicate glass particles, with the reactive glass being the minor phase. In contrast to glass ionomers, compomers do not contain significant amounts of water. The sole initial curing reaction is radical induced polymerization of the acrylic resin monomer matrix. An acid-base reaction takes place between TCB and the ion leachable fluorosilicate glass only after water infuses the cured composite via exposure to oral fluids, which also causes the filling to release fluoride ions. Flexural strength values of 90–125 MPa have been reported for compomers (Hickel, *Acad Dent Mater Trans* 9: 105, 1996). However, these strength values are still inferior to those of current dental amalgam (110–150 MPa) and composite resins (100–145 MPa) (Hickel, *Acad Dent Mater Trans* 9: 105, 1996). Therefore, compomers are currently not recommended for use in large, stress-bearing posterior applications.

2.c Problems in Current Materials

Two major problems have been overlooked in the current research and development of dental composite resins, glass ionomers, resin-modified glass ionomers and compomers. The first problem is that, glasses and glass-ceramics are among the weakest and most brittle materials to use as reinforcement fillers. Glass filler particles are sensitive to surface flaws produced during mixing, handling and wear. A crack in the resin matrix can easily cut through the reinforcing glass particles (lower arrow in FIG. 1). The second problem is related to the geometrical shapes of the filler particles. The current glass fillers are either spherical or of irregular shapes, with length-to-diameter ratio only slightly larger than one. This has at least two major short-comings. First, rounded filler particles at occlusal surfaces are susceptible to facile dislodgement from the resin matrix during wear with foods bolus, resulting in high wear rates. Second, if a crack is initiated in the composite, it can easily propagate around the filler particles (upper arrow in FIG. 1), hence causing the reinforcing effect of the filler particles to be lost.

2.d This Invention: Whisker Reinforcement

There is a need to overcome the problems described above. The present invention uses ceramic whisker reinforcement to improve the mechanical properties of dental composite resins, glass ionomers, resin-modified glass ionomers, and compomers. The term "whisker" is used to include the following fillers of elongated shapes: (1) ceramic single-crystalline whiskers, such as silicon nitride, silicon carbide, mullite, zirconia, sapphire; (2) chopped fibers, including ceramic such as silicon carbide, silicon nitride, alumina, zirconia, carbon, glass fibers, and polymer fibers. The diameter of the whiskers and chopped fibers ranges from 0.1 $\mu$m to 300 $\mu$m, preferably from 0.2 $\mu$m to 20 $\mu$m. The length of the whiskers and chopped fibers ranges from 1 $\mu$m to 10 mm, preferably from 5 $\mu$m to 1 mm, most preferably from 5 $\mu$m to 50 $\mu$m.

This invention further uses silicate filler particles to bond onto the surfaces of individual whiskers or chopped fibers to: (1) improve the efficacy of whisker and chopped fiber silanization and bonding with the matrix; (2) separate the whiskers and chopped fibers from each other, thereby preventing entanglement; and (3) enhance the retention of the whiskers and chopped fibers in matrix by providing rougher particle-bonded surfaces of the whiskers and chopped fibers.

Any glassy or crystalline silicate-containing particles can be used, including dental microfill glass, hybrid glass, quartz, silicon nitride, silicon carbide, and glass ceramics, with particle diameter ranging from 0.01 $\mu$m to 100 $\mu$m, preferably from 0.03 $\mu$m to 10 $\mu$m.

In the past, single-crystalline whiskers have been used to reinforce ceramics (e.g., Becher and Wei 1984, *J Am Ceram Soc* 12: C267–269; Hirata et al., 1989, *J Ceram Soc Jpn* 97: 866–871) and metals, Bose et al. 1994, U.S. Pat. No. 5,116,004). Certain plastics (or resins) have also been reinforced with ceramic whiskers. Whisker-reinforced plastics have been proposed for use in applications including electrical (Robeson and Harris, 1986, U.S. Pat. No. 4,613,645), golf club head (Tominaga and Sasaki, 1987, U.S. Pat. No. 4,687,205), and orthodontic bracket (Carberry and Negrych, 1992, U.S. Pat. No. 5,078,596). However, single-crystalline whiskers have not been used to reinforce dental direct filling or indirect polymeric composites, glass ionomers, resin-modified glass ionomers or compomers.

Further, in the past, chopped glass fibers and crystalline fibers and polymer fibers have been used to reinforce certain polymers (Grant and Greener, *Aust Dent J* 12: 29, 1967; Skirvin et al., *Military Med* 147: 1037, 1982; Krause et al., *J Biomed Mat Res* 23: 1195–1211, 1989; Williams et al, 1992, *Dent Mater* 8: 310–319; Bayne and Thompson, 1996 *Academy Dent Mater* 9: 238). However, silicate particle fillers have not been used to mix with chopped fibers to disperse the fibers preventing entanglement, and the individual chopped fibers have not been bonded or coated with silicate filler particles to improve filler distribution and enhanced retention in the matrix. This is likely why dental composites reinforced with chopped fibers have not showed significant improvements over silicate particle reinforced composites (Williams et al, 1992, *Dent Mater* 8: 310–319; Bayne and Thompson, 1996 *Academy Dent Mater* 9: 238).

To conclude, in the past, single-crystalline ceramic whisker and polycrystalline chopped fibers and glass chopped fibers and polymer fibers have not been individually bonded or coated with silicate filler particles and/or ion-releasing fluorosilicate glasses to reinforce dental polymeric composites, glass ionomers, resin-modified glass ionomers and compomers. Further, single-crystalline ceramic whisker and polycrystalline chopped fibers and glass chopped fibers and polymer fibers have not been mixed with ion-releasing fluorosilicate glasses and/or polyacid and/or powdered pre-cured glass ionomers and/or powdered pre-cured resin-modified glass ionomers to reinforce dental materials.

SUMMARY OF THE INVENTION

This invention provides a new generation of dental materials with polymeric composites on one end of the material spectrum, glass ionomers on the other end, and resin-glass ionomer hybrid materials such as compomers and resin-modified glass ionomers intermediary in the spectrum, that possess greatly improved strength and toughness, and substantially improved resistance to wear, micro-cracking, fracture and fatigue.

The invention includes the use of ceramic filler particles and whiskers and/or chopped fibers to reinforce polymeric dental composites so that there are substantially improved mechanical properties and enhanced clinical longevity compared to conventional (or currently used) materials. The elongated whiskers and chopped fibers have high length-to-diameter ratio values to effectively bridge and resist micro-cracks, and are less likely to be dislodged out of the matrix during wear.

The invention includes a method of preparing reinforced polymeric dental restorative materials with selected whiskers and/or chopped fibers that are silanized to efficiently bond these reinforcements to dental matrix resins when cured. The invention further includes a method of preparing reinforced polymeric dental restorative materials by forming a surface layer of silicon dioxide ($SiO_2$) on specific individual whiskers or chopped fibers for effective silanization to bond to the dental matrix material. The invention further includes a method of dispersing the whiskers or chopped fibers from each other to avoid whisker entanglement and to improve filler packing, by mixing the whiskers/fibers with silicate filler particles. The invention further includes a method of preparing reinforced polymeric composites by bonding silicate filler particles onto the surface of the individual whiskers or chopped fibers prior to silanization for effective silanization and improved retention in matrix by providing rougher whisker/fiber surfaces.

This invention further includes a method of mixing the whiskers or chopped fibers with reactive ion-releasing fluorosilicate glass particles and polyacid to be used as fillers in composites for fluoride release.

This invention further includes a method of mixing the whiskers or chopped fibers with powdered pre-cured glass ionomers and/or powdered pre-cured resin-modified glass ionomers to be used as fillers in composites for fluoride release.

This invention still further includes methods of bonding reactive ion-releasing fluorosilicate glass particles onto the individual whiskers or chopped fibers to react with polyacids to release fluoride and to better bond and retain the whiskers or chopped fibers in the matrix.

The inventive method described and claimed herein results in a series of reinforced dental materials, with polymeric composites at one end of a material spectrum, glass ionomers at the other end, and hybrids such as resin-modified glass ionomers and compomers intermediary in the spectrum, that are particularly useful for dental filling, inlay, crown, adhesives, bases, liners, luting agents, and core buildup applications with substantially improved mechanical properties, including strength, fracture toughness, and resistance to micro-cracking and wear.

An object of the present invention is to provide a method of reinforcement for a spectrum of dental materials, with polymeric composites at one end of the spectrum, glass ionomers at the other end, and hybrids such as resin-modified glass ionomers and compomers intermediary in the spectrum.

A further object of the present invention is to provide a method of preparing polymeric dental restorative materials, compomers, resin-modified glass ionomers and glass ionomers with ceramic filler particles and whiskers and/or chopped fibers to provide reinforcement.

A further object is to provide a method of dispersing the whiskers and/or chopped fibers from each other to avoid entanglement and to improve the filler packing using bimodal or trimodal distribution by the mixing of whiskers and/or chopped fibers with particulate fillers.

A further object of the present invention is to provide a method of preparing a reinforced dental material with silicate filler particles bonded onto the surfaces of individual whiskers or chopped fibers for effective silanization, improved whisker/fiber distribution, and enhanced retention in matrix resin by providing rougher whisker/fiber surfaces.

A further object of the present invention is to provide a method of preparing reinforced dental compomers, resin-modified glass ionomers and glass ionomers by mixing ion-releasing fluorosilicate glass with whiskers and/or chopped fibers.

A further object of the present invention is to provide a method of preparing reinforced compomers, resin-modified glass ionomers and glass ionomers by bonding ion-releasing fluorosilicate glass particles onto the individual whiskers and/or chopped fibers.

A further object of the present invention is to provide a method of preparing reinforced composites and compomers with fluoride release by mixing or bonding silicate and/or reactive fluorosilicate particles with whiskers and/or chopped fibers, then mixing such whiskers and/or chopped fibers with powdered pre-cured glass ionomers, and/or powdered pre-cured resin-modified glass ionomers, and/or polyacid and reactive fluorosilicate glass.

Another object of the present invention is to provide a method of preparing improved reinforced polymeric dental restorative materials, compomers, glass ionomers and resin-modified glass ionomers to form dental composites, for example, cements, core-buildups, fillings, inlays, onlays, crowns and bridges.

Another object is to provide a method of fabricating stronger dental restorations by laminating whisker and/or chopped fiber reinforced composite resins, compomers, and glass ionomers underneath conventional dental materials.

Further objects and advantages of the invention include the improved reinforced polymeric dental restorative material prepared by the new methods, the methods of using the reinforced dental restorative materials, and the products made from those embodying the characteristics set forth above.

DETAILED DESCRIPTION OF THE INVENTION

Figure 1:
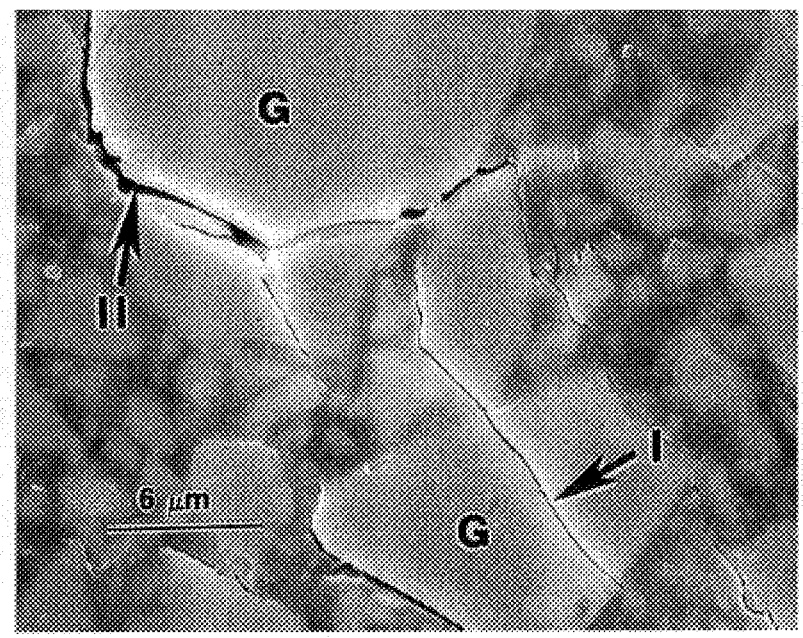
FIG. 1 is scanning electron micrograph (SEM) showing problems with current dental composite resins, compomers, resin-modified glass ionomers and glass ionomers. Matrix cracks cut through the glass filler particle or propagate around the round-shaped fillers. In both cases, the reinforcing effect of the fillers is lost.

The inventive reinforced dental materials, with composite resins at one end of the material spectrum, glass ionomers at the other end, and resin-modified glass ionomers and compomers intermediary in the spectrum, fabricated using the method of the present invention, possess mechanical properties, including strength, fracture toughness and resistance to micro-cracking, which are substantial improvements over conventional dental materials. In conventional systems, glass filler particles have been used for reinforcement. The glassy nature of the filler particles render them brittle and susceptible to fracture, the rounded shapes of the filler make them inefficient in stopping a micro-crack from propagation and in resisting dislodgment of the filler particles during wear.

In the reinforcement technology of the present invention, whiskers and/or chopped fibers are mixed or bonded or fused with silicate particles and used to reinforce dental materials. The superior strength properties of these whiskers and/or chopped fibers make them extremely resistant to fracture. Further, the elongated shapes of the whiskers/chopped fibers enable effective bridging of cracks and resist dislodgment during wear. Further, silicate particles can be bonded or fused onto the surfaces of the individual whiskers or chopped fibers. They not only improve the effectiveness of the silanization, but also enhance the whisker retention in matrices due to the rougher surfaces of the silicate particle-fused whiskers or chopped fibers. Both direct and indirect dental composite restorations can be fabricated by using different types of whiskers and/or chopped fibers, silicate filler particles and dental material matrices.

I. Composite Resins

If the composite resin is opaque, chemical curing can be performed. Further, light curing can be utilized if the refractive index of the resin can be adjusted to match that of the whiskers and/or chopped fibers. The reinforced polymeric dental restorative materials of the present invention can be formed into dental restorations selected from the group consisting of fillings, inlays, onlays, bridges, and crowns. These whisker-reinforced dental composites have substantial advantages over conventional dental composites, exhibiting high flexural strength, high compressive strength, high work-of-fracture and toughness, greater resistance to micro-cracking and better retention of fillers in resin matrices during wear.

Curing, as defined in the present invention, means the hardening of a material from a liquid paste to a hard solid by means of chemical reactions involved in the polymerization process. Curing can be accomplished by many conventional methods: chemical curing results when a two-paste or a powder/liquid formation is mixed, causing a chemical reaction that hardens the composite; light curing, in which the polymerization is initiated photochemically by ultraviolet or visible light, may also be utilized. In one paste formulation, the resin ingredient is subjected to a light beam for curing; dual curing involving both chemical curing and light curing may be used; direct curing involving any of the foregoing curing methods without the application of additional heat or pressure may also be utilized in the present invention; and indirect curing involving any of the first three foregoing curing methods with the addition of heat and/or pressure. The conditions of applying of the additional heat and pressure would be known to a worker skilled in the art, depending upon the materials being cured.

When referring to silanization in the present invention, it is meant that the filler is surface-treated with a thin film of reactive siloxane on the individual fillers, one end of which bonds to the filler while the other end bonds to the matrix. Any of the currently used silane chemicals and processes known to one skilled in the art can be used, according to the specific filler and matrix resin types that are to be used in the composite. For example, for dental resins and silicate fillers, 3-methacryloxpropyltrimethoxysilane (MPTMS) may be used in the process of the invention. Un-silanized fillers can also be incorporated into the composites.

The term "dental monomers" means dental matrix resins before polymerization. All the dental resins currently available or under development can be reinforced with whiskers to improve mechanical strength and toughness. Examples of dental resins are 2,2-bis[p-(2'hydroxy-3'-methacrylatephenly] propane tri(ethylene glycol) dimethacrylate designated as Bis-GMA, and TEGDMA, and UDMA, or mixtures thereof. Further examples are a mixture with the amount of Bis-GMA to TEGDMA usually ranging from about 99:1 to 1:90, preferably from 70:30 to 30:70, by weight. The amounts of resins and fillers vary with the intended application. The amount of resin typically in the composition is about 10% to about 90%, preferably about 20% to about 60% by weight.

In accordance with the present invention, silicate filler particles are defined herein as ceramic particles from the silicon-containing group, including various types of silicate glass, ion-releasing fluorosilicate glass, glass-ceramics, quartz, silicon nitride, silicon carbide, dental microfill glass, hybrid glass, powdered pre-cured glass ionomers, powdered pre-cured composite resins, and various mixtures of the above particles. Typically, silicate filler particles are of rounded or irregular shapes with a length-to-diameter ratio of less than 5, and a diameter ranging from 0.01 $\mu$m to 100 $\mu$m, preferably from 0.03 $\mu$m to 30 $\mu$m.

In accordance with the present invention, whisker fillers are defined by those conventional whiskers available currently and under development. They may be classified in groups. Group 1 whiskers comprise ceramic single-crystalline whiskers. All types of single-crystalline whiskers may be included in this category, e.g., silicon nitride, silicon carbide, mullite, sapphire, or mixtures of different types of whiskers. The length-to-diameter ratio of the whiskers ranges from 2 to 100, preferably from 5 to 20. Group 2 comprises chopped fibers of polycrystalline, single-crystalline, glass, polymers, and metals. All types of fibers including ceramic, glass, organic fibers, or mixtures of different fibers, can be utilized in the present invention. The length to diameter ratio of the chopped fibers usually ranges from 2 to 1000, preferably from 10 to 300. Further, Group 3 comprises mixtures of the first two groups at various ratios ranging from 1:99 to 99:1.

Generally, in the present invention, the preparation of reinforced dental material relates to three general, pretreatment processes before the fillers are silanized and incorporated into resins to form the composite material. The first type of pretreatment involves the surface treatment of any type of whisker fillers to form a surface silicon dioxide ($SiO_2$) layer before silanization. The surface silicon dioxide layer may be formed by conventional chemical reactions, usual coating/sputtering methods, or by heat treatment in a heat treatment environment with air or oxygen at a temperature between 100° C. to 1600° C. at a time ranging from about 5 minutes to about 24 hours. The surface-treated whisker fillers are then silanized or otherwise surface-treated or left unsilanized, and incorporated into resin monomers and cured to make composites.

The second pretreatment process involves the bonding of whisker fillers with particulate filler from groups 1, 2 and 3 as well as those whisker fillers pretreated with a silicon dioxide layer. The purpose of bonding with particulate fillers is to disburse the whiskers or chopped fibers away from each other to avoid entanglement, to enhance the efficacy of silanization and to improve the retention in resin matrix by providing rougher surfaces on the whiskers and chopped fibers. The bonding can be performed by using any currently available bonding and coating and sputtering and deposition techniques, including, but not limited to, high temperature fusion, which is known to skilled workers in the art. In the case of high temperature fusion, the temperature can be within the range of about 150° C. to 1600° C. for a time period of about 5 minutes to about 24 hours. Particle fillers than can be bonded or coated onto the individual whiskers are various silicate or silica filler particles as described. For example, dental microfill, hybrid, and macrofill silicate fillers can be utilized. The weight ratio of the whisker: particulate fillers is from about 5:95 to 95:5, preferably from 30:70 to 70:30. The particulate bonded whisker fillers are silanized and then incorporated into resin monomers and cured to make composites.

The third pretreatment involves the mixing of particulate fillers with any of whisker fillers in groups 1, 2 or 3 and whisker fillers that have been treated with the surface silicon dioxide layer or those whisker fillers which are bonded to particulate fillers. The purpose of mixing with particulate fillers is to disperse the whiskers or chopped fibers away from each other to avoid entanglement, and to improve filler packing with bimodal or trimodal distributions. All the silicate particle fillers as described earlier in this invention can be used. Further, ceramic particles that do not contain silicon, such as alumina, zirconia, can also be used to mix with the whiskers. Still further, ground pre-cured composite particles may also be utilized as particulate fillers to be mixed with the whiskers. Polymeric composites, for example hybrid glass-filled composite resin, are cured, then ground into powders. The particle size can vary from about 0.01 $\mu$m to about 100 $\mu$m. The weight ratio of whisker: particulate fillers ranges from about 5:95 to about 95:5. The mixture of whisker fillers and particulate fillers are silanized or unsilanized and incorporated into resin monomers and then cured to make composites. These pretreatment processes are further defined in additional embodiments.

The elongated whiskers, for example, ceramic single-crystalline whiskers, typically have a length to diameter ratio greater than 5. At this size, the the fillers effectively bridge and resist micro-cracks and are less likely to be dislodged out of the resin matrix during wear. Typically the whiskers, for example silicon nitride whiskers, will have preferred diameters ranging from 0.1 $\mu$m to about 5 $\mu$m and lengths ranging from about 1 $\mu$m to about 50 $\mu$m. Typically, silicon carbide whiskers have an average diameter of approximately 0.1 to 2 $\mu$m and a length of about 1 to 50 $\mu$m. Typically, chopped polycrystalline or glass fibers have an average diameter of approximately 5 to 100 $\mu$m and a length of about 50 $\mu$m to 3 mm preferably 50 $\mu$m to 1 mm.

Figure 2:
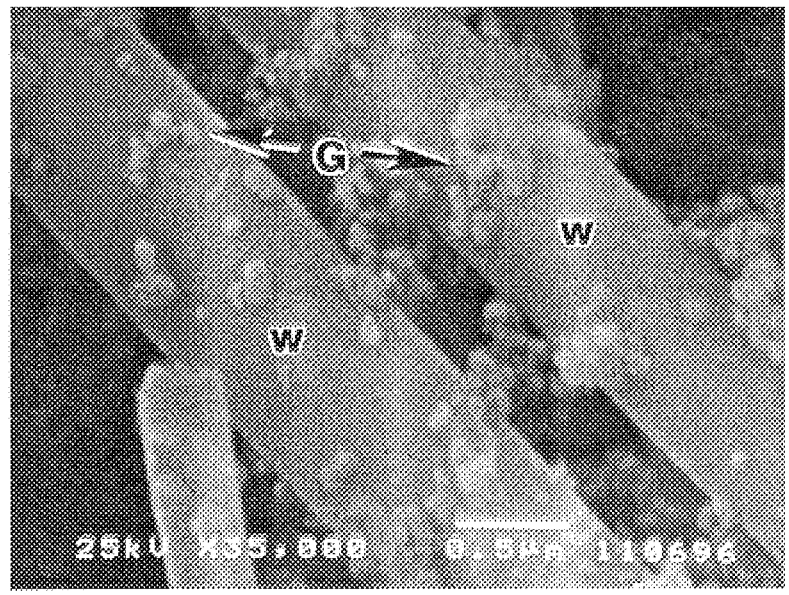
FIG. 2 is an SEM micrograph of silicate particles "G" bonded onto the whiskers "W" produced in the present invention. This provides the ease of silanization for all types of whiskers due to the bonded silicate ($SiO_2$-containing) particles, disperses the whiskers preventing entanglement, improves the filler loading due to bimodal distribution, and enhances the retention of whiskers in the matrix by providing rougher whisker surfaces.

As an example, FIG. 2 shows silicate particle-bonded whiskers in a scanning electron micrograph in which the dental microfill glass particles, which are fumed silica, are fused onto silicon nitride whiskers by heat treatment. The glass particles "G" are bonded onto the whiskers "W". This disperses the whiskers preventing whisker entanglement, enhances silanization and hence chemical bonding to the resin matrix, and further improves the whisker retention in matrix resin by providing rougher whisker surfaces.

In one embodiment, a general method of the preparation of whisker and/or chopped fiber reinforced dental composites is shown by selecting whiskers that are either directly silanized, or surface treated and then silanized. The surface treatment relates to coating the whiskers with silicate or silica particles. Silanization is performed using the usual silane coupling agents and processes as in current composite resin technology. The silanized or un-silanized whisker-silicate powders are then mixed with dental resin monomers and cured. Curing involves either light curing, chemical curing, or dual curing, in the usual way.

Another embodiment of the invention is the use of silicon-containing whiskers, for example silicon nitrite, silicon carbide, and mullite, to reinforce dental resins. Mullite whiskers contain silicon dioxide and can be directly silanized. The silicon nitride whiskers and the silicon carbide whiskers can form a silicon dioxide layer on the whisker surface by controlled heat treatment in air or in oxygen. The heat treatment typically takes place at a temperature of about 150° C. to about 1600° C., preferably 300° C. to 1000° C. The silicon dioxide coated whiskers are silanized to bond to the dental matrix resin. The silanization process is performed as previously described. The silanized or un-silanized whiskers are mixed with dental resin monomers and then cured as previously described.

Another embodiment of the present invention relates to the use of a mixture of whiskers and silicate particles (e.g., silicate glass, glass-ceramics, quartz) to reinforce dental resins. Whiskers are mixed with silicate particles to form bimodal or trimodal distributions. The use of silicate particles help separate the whiskers to prevent entanglement. The silicate particles are selected from the group consisting of silicon as previously described. A silicon dioxide layer is first formed to the whisker surface as previously described. The whiskers are then mixed with a prescribed amount of silicate filler powders by dispersing in an agitated liquid. The ratio of whisker-to-silicate filler by weight ranges from 95:5 to 5:95, preferably from 30:70 to 70:30. The dried mixture is then silanized or un-silanized, mixed with dental resin monomers and cured.

Another embodiment of the present invention relates to the use of silicate particles coated or bonded onto the individual whiskers to reinforce dental resins. The silicate particles are bonded onto the surfaces of individual whiskers for enhancing the silane bonding and improving the retention of whiskers in resin matrices by providing a rough whisker surface. The whiskers can be any type of whiskers and mixtures of different types of whiskers for better distribution and packing. The silicate particles may be selected from the group consisting of silicon as previously described. As an example, a prescribed amount of whiskers such as silicon nitride or silicon carbide are mixed with a prescribed amount of silicate powders, for example microfill glass, by dispersing in a beaker or flask with a liquid, such as ethyl alcohol or other suitable dispersant. The solution is thoroughly stirred to mix the glass particles with the whiskers while heated to dryness at temperatures of about 30° C. to 300° C. The dried whisker-glass mixture is then heat treated in a furnace in air at a temperature of about 500° C. to 1600° C., preferably from 600° C. to 1000° C., or in a controlled atmosphere, such as under nitrogen gas, to fuse the glass particle onto the surfaces of the individual whiskers. The fused glass-whisker powders are silanized or left un-silanized, mixed with dental resin monomers and cured.

Another embodiment of the present invention relates to reinforcing dental resins with yet other types of whiskers, for example mullite, sapphire, potassium titanate, and aluminum nitride, as well as those types under development. Various types of silicate or silica particles as described previously can be used to bond onto the surfaces of the individual whiskers to facilitate silanization and to provide better retention of rough surface whiskers in resin matrices.

Yet another embodiment of the present invention involves the use of various types of chopped fibers or whiskers mixed with chopped fibers to reinforce dental resins. The different types of whiskers and chopped fibers are mixed together to provide better packing by bimodal distribution and, therefore, higher filler levels. Silicate filler particles can be used to bond onto the surfaces of the individual whiskers and the chopped fibers to facilitate the silanization and to provide retention of the rough-surfaced whiskers and chopped fibers in resin matrices.

Still in another embodiment, the reinforced dental resin can be fabricated into dental composite restorations. Dental polymeric composite restorations reinforced with whiskers and/or chopped fibers, such as fillings, inlays, onlays, crowns, and bridges can also be fabricated by using the same procedures for whisker surface treatments and whisker silicate particle mixing and fusion as described above. An aesthetic shading can be coated onto the outer surfaces of the restorations if needed. The shading layer can also be used to prevent direct contact of whiskers with opposing enamel to prevent excessive wear of enamel. With no intention of being limiting, the shading layer may be a conventional dental composite resin such as microfill or hybrid composite resin.

II. Compomers, Resin-modified Glass Ionomers and Glass Ionomers

This part of the invention consists of three new technologies for processing reinforced dental compomers, glass ionomers and resin-modified glass ionomers: (1) whisker and/or chopped fiber reinforcement of conventional compomers, glass ionomers and resin-modified glass ionomers; (2) whisker and/or chopped fiber mixed with ground pre-cured glass ionomer powder to form reinforced dental composites; (3) whisker and/or chopped fiber, ionomer glass and polyacid powder to form reinforced dental composites. (2) and (3) differ from (1) in that in (2) and (3), no carboxylic acid resin is needed as a liquid component (although it can be part of the resin system), and all the fillers (including whiskers, ground pre-cured glass ionomer, reactive fluor-glass, and polyacid powder) are silanized, although un-silanized fillers can also be used. (2) differs from (3) in that pre-cured glass ionomer powders are used in (2), and un-cured reactive fluor-glass and polyacid powders are used in (3). This invention will make available a new generation of dental compomers, glass ionomers and resin-modified glass ionomers with mechanical strength and toughness that greatly exceed those of the currently used compomers, glass ionomers and resin-modified glass ionomers, without compromising the contents of reactive ion-releasing fluorosilicate glass and polyacid, and hence the capacity for fluoride release.

The following are illustrations of the complete operational cycles of this part of the invention. Other useful configurations will be familiar to those skilled in the art.

An illustration of a complete operational cycle for part (1), whisker-reinforcement of conventional compomers, glass ionomers and resin-modified glass ionomers, is given in the following. Ceramic whiskers (single-crystalline, e.g., silicon carbide, silicon nitride, mullite, sapphire; or chopped fibers, e.g., polycrystalline fibers, glass fibers) are mixed with dental silicate particles (e.g., microfill glass, hybrid glass, quartz, glass-ceramics, ion-releasing fluor-glass) at a prescribed whisker to glass weight ratio ranging from 5% to 95%, preferably from 20% to 80%. The whisker or chopped fiber diameter can range from 0.1 to 50 $\mu$m, preferably from 0.3 to 20 $\mu$m, with a length to diameter ratio ranging from 2 to 1000, preferably from 5 to 100. The silicate filler particles are then bonded onto the whiskers or chopped fibers by usual coating or deposition techniques or bonding methods, including, but not limited to, high temperature fusion. In high temperature fusion, the whisker-silicate filler mixture is heat-treated at a sufficiently high temperature, ranging from 600° C. to 1400° C., preferably 700° C. to 1000° C., to fuse the silicate particles onto the individual whiskers. In the case of compomers, the silicate filler-coated whiskers are then silanized in a usual way, for example, by mixing with 3-methacryloxypropyltrimethoxysilane (MPTMS) in an appropriate solvent. The silanized particle-bonded whiskers are then mixed with reactive fluoride-releasing glasses at a prescribed weight ratio (e.g., 5:1, 4:1, 1:1) and used as fillers for dental resins. Two-part chemical curing or one-part light curing in usual ways can be performed to harden the restorations. Only as an illustration of two-part chemical curing, a dental resin monomer, containing Bis-GMA and TEGDMA at a 1:1 weight ratio, is divided into two equal parts. Part I is mixed with a weight fraction of 0.05% BHT and 2% benzoyl peroxide (BPO), designated as resin monomer I. Part II (resin monomer II) is mixed with 1% of dihydroxyethyl-p-toluidine (DHEPT). Each resin monomer is then mixed with a carboxylic acid monomer (methacryloyloxyethyl phthalate, or MEP), at a resin/MEP weight ratio of 4:1. Equal weight fractions of fillers (containing reactive fluoride-releasing Sr-glass and whiskers) are then blended with the two liquids to form compomer pastes I and II, respectively. To test the mechanical properties, the two pastes can be mixed thoroughly and filled into a steel mold of dimension 2 mm×2 mm×25 mm to make flexural specimens. The specimens can then be incubated at 37° C., either dry or in distilled water, for 24 hours prior to mechanical fracture testing. In the case of resin-modified glass ionomers, the silicate and/or ion-releasing fluor-glass particle-coated whiskers or chopped fibers are mixed with an ion-releasing fluor-glass, then blended with a resin-modified glass ionomer liquid and/or powder and cured as usual. In the case of glass ionomers, the silicate and/or ion-releasing fluor-glass particle-coated whiskers or chopped fibers are mixed with a ion-releasing fluor-glass, then blended with a glass ionomer liquid or water and/or polyacid powder and cured as usual for glass ionomers.

An illustration of a complete operational cycle for part (2) is given in the following. Ground pre-cured glass ionomer particles are obtained by grinding pre-cured glass ionomer or resin-modified glass ionomer into powders. A glass ionomer cement is cured by mixing a commercial powder of a reactive ion-releasing fluorosilicate glass and polyacid with water. The powder to liquid weight ratio ranges from 1:1 to 7:1, preferably 4:1 to 6:1. The mixed paste is filled into a steel mold with a cavity of 2 mm ×2 mm×20 mm and cured at 37° C. for 24 hours. The cured glass ionomer specimens are then ground into powders by mortar and pestle or other usual ways. Ceramic whiskers or chopped fibers are coated with silicate as described in the above paragraph. The silicate-bonded whiskers or fibers are then mixed with the pre-cured ground glass ionomer or resin-modified glass ionomer powders and silanized, and then blended with dental resin monomers and cured. As an example of blending with dental resin and curing, a dental resin monomer, containing Bis-GMA and TEGDMA at a 1:1 weight ratio, is divided into two equal parts. Part I is mixed with a weight fraction of 0.05% BHT and 2% benzoyl peroxide, designated as monomer I. Part II is mixed with 1% of dihydroxyethyl-P-toluidine (monomer II). Equal weight fraction of fillers (containing ground pre-cured glass ionomer particles and ceramic whiskers) are then mixed with monomers I and II to form pastes I and II, respectively. The two pastes are then mixed thoroughly and filled into a steel mold of dimension 2 mm×2 mm×25 mm. Each specimen can be incubated at 37° C. for 24 hours and then demolded.

An illustration of a complete operational cycle for part (3) is given in the following description. An anhydrous blended glass ionomer powder, which is, as usual, a mixture of reactive ion-releasing fluorosilicate glass and powdered polyacid, is used. Ceramic whiskers or chopped fibers are coated with silicate as described. The silicate-coated whiskers are then mixed with the glass ionomer powder containing reactive ion-releasing fluorosilicate glass and powdered polyacid, at weight fractions ranging from 10% to 90%, preferably 30% to 70%. The mixture is then silanized, blended with dental resin monomers and cured, as usual. As an illustration, chemical curing based on a two-paste formulation as that described in the above paragraph, can be performed.

The silicate particles to be coated onto the whiskers can be microfill glass, macrofill glass, hybrid glass, glass-ceramic, quartz, ion-releasing fluor-glass or all other types of silicate particles or mixtures of different particles. All types of whiskers or chopped fibers available (e.g., silicon nitride, silicon carbide, mullite, sapphire, titanium nitride, alumina, glass, etc.), and many under development, can be used. All types of reactive ion-releasing fluorosilicate glass available and many under development, all types of compomer and glass ionomer and resin-modified glass ionomer powder and/or liquid available and many under development, and all types of dental resin monomers available and many under development, can be used.

One embodiment would be the use of silicon-containing ceramic whiskers (single-crystalline whiskers, such as silicon nitride, silicon carbide, mullite, or polycrystalline chopped fibers, or chopped glass fibers) to reinforce dental compomers that utilize reactive fluorosilicate glass and acidic polymerizable monomers. These silicon-containing whiskers or chopped fibers can be either directly silanized, or a surface silicon dioxide ($SiO_2$) layer can be formed onto the whiskers before silanization. Such surface silicon dioxide ($SiO_2$) layer can be formed onto the whiskers or chopped fibers by techniques including, but are not limited to, high-temperature surface oxidation of the silicon-containing whiskers or chopped fibers. The silanized whiskers are then mixed with reactive ion-releasing fluorosilicate glass particles. The mixed powder is blended with a usual liquid of resin monomers and acidic polymerizable monomers and then cured, in the usual manner as for current dental compomers. Light curing can be used if the material is translucent enough; otherwise two-part chemical curing can be performed. Dual (photochemical plus chemical) curing is also an option. All types of silicon-containing whiskers or chopped fibers available and many under development, all types of reactive ion-releasing fluorosilicate glass available and many under developement, and all types of compomer liquid or powder containing resin monomers and acidic polymerizable monomers available and many under development, can be used.

Another embodiment would be mixing the silicon-containing ceramic whiskers or chopped fibers with silicate particles to reinforce currently used dental compomers that utilize reactive fluorosilicate glass and acidic polymerizable monomers. Silicate particles include, but are not limited to, dental silicate particles such as microfill glass, hybrid glass, quartz, glass ceramics. The purpose of mixing the whiskers or chopped fibers with silicate particles is: (1) to use the silicate particles to disperse the individual whiskers from each other avoiding whisker entanglement; (2) to improve the filler distribution and to increase the filler level in the matrix with bimodal distributions; and (3) to improve the esthetics of the resultant material due to increased silicate content and decreased whisker content. The silicon-containing whiskers or chopped fibers are mixed with prescribed amount and composition and size of silicate particles. The whisker-silicate particle mixture is then silanized. The silanized powder is then mixed with reactive ion-releasing fluorosilicate glass particles. The mixed powder is blended with a liquid of resin monomers and acidic polymerizable monomers and then cured, in the same manner as usually used dental compomers. Light curing can be used if the material is translucent enough; otherwise two-part chemical curing can be performed. Dual (photochemical plus chemical) curing is also an option. All types of silicon-containing whiskers or chopped fibers available and many under development, all types of reactive ion-releasing fluorosilicate glass available and many under development, and all types of dental resin monomers available and many under development, can be used.

Another embodiment would be the use of silicate particle-bonded whiskers or chopped fibers to reinforce dental compomers that utilize reactive fluorosilicate glass and acidic polymerizable monomers. The silicate particles are coated onto the surfaces of individual whiskers or chopped fibers for the purpose of (1) enhancing the silane efficacy hence whisker-matrix bonding; (2) improving the filler distribution and avoiding whisker entanglement; and (3) enhancing the retention of whiskers in matrices by providing rougher whisker surfaces. The silicate particle-whisker bonding can be achieved by elevated-temperature fusion or by other bonding or deposition techniques. The silicate particle-fused whiskers or chopped fibers are then silanized. The silanized powder is then mixed with reactive ion-releasing fluorosilicate glass particles. The mixed powder is blended with a liquid of resin monomers and acidic polymerizable monomers and then cured, in the same manner as usually used for dental compomers. Light curing can be used if the material is translucent enough; otherwise two-part chemical curing or dual curing can be performed. The silicate particles to be fused onto the whiskers can be microfill glass, macrofill glass, hybrid glass, glass-ceramic, quartz, and all other types of silicate particles or mixtures of different particles. All types of whiskers or chopped fibers available (e.g., silicon nitride, silicon carbide, mullite, sapphire, titanium nitride, alumina, glass, etc.), and many under development, can be used. All types of reactive ion-releasing fluorosilicate glass available and many under development, and all types of resin monomers available and many under development, can be used.

Another embodiment would be the use of ceramic whiskers (single-crystalline whiskers, such as silicon nitride, silicon carbide, mullite, or polycrystalline chopped fibers, or chopped glass fibers) to reinforce dental resin-modified glass ionomers. These whiskers or chopped fibers can be either as-received, or a surface silicon dioxide ($SiO_2$) layer can be formed onto the whiskers, or mixed with silicate fillers for improved distribution, or bonded with silicate filler particles, as described in examples 1–3. The whiskers are mixed with reactive ion-releasing fluorosilicate glass particles. The mixed powder is blended with a liquid of a usual resin-modified glass ionomer, such as a liquid mixture of water, polyacid and resin monomer. The paste can then be light cured or chemically cured, together with the acid-base reaction as in a usual resin-modified glass ionomer. All types of ceramic whiskers or chopped fibers available and many under development, all types of reactive ion-releasing fluorosilicate glass available and many under development, and all types of resin-modified glass ionomer liquid or powder available and many under development, can be used.

Another embodiment would be the use of ceramic whiskers (single-crystalline whiskers, such as silicon nitride, silicon carbide, mullite, or polycrystalline chopped fibers, or chopped glass fibers) to reinforce dental glass ionomers. These whiskers or chopped fibers can be either as-received, or a surface silicon dioxide ($SiO_2$) layer can be formed onto the whiskers, or mixed with silicate fillers for improved distribution, or bonded with silicate filler particles. The whiskers are mixed with reactive ion-releasing fluorosilicate glass particles. The mixed powder is blended with a liquid of a usual glass ionomer, such as a liquid mixture of water and polyacid. The paste is then cured by an acid-base reaction as in usual glass ionomers. If the polyacid is in a powdered state, the whisker-ionomer glass mixture is further mixed with polyacid, then with water and cured by acid-base reaction. In more preferred cases, the ionomer reactive glass particles are bonded onto the surfaces of whiskers and/or chopped fibers (e.g., by high temperature fusion); the mixture is then blended with a usual ionomer liquid containing water and polyacid and cured by acid-base reaction. If the polyacid is in a powdered state, the whisker-ionomer glass mixture is further mixed with polyacid, then with water and cured by acid-base reaction. All types of ceramic whiskers or chopped fibers available and many under development, all types of reactive ion-releasing fluorosilicate glass available and many under development, and all types of glass ionomer liquid or polyacid powders available and many under development, can be used.

Besides the incorporation of whisker or chopped fiber reinforcement into the conventional compomer technology that utilize reactive fluor-glass and acidic polymerizable monomers, another embodiment would be to fill dental resins with whiskers and ground powders from pre-cured glass ionomer or resin-modified glass ionomer cements. In this technology, the whiskers or chopped fibers and the ground pre-cured glass ionomer powder mixture is silanized and blended with dental resin monomers and cured. The silane agents and the dental resins can be the same as those of the dental composite resins available or under development. The "whiskers" can be silicon-containing whiskers or chopped fibers, or whisker-silicate particle mixtures, or silicate particle-coated whiskers. All the whiskers and chopped fibers available, and many under development, can be used. The ground pre-cured glass ionomer or resin-modified powders can be obtained by first making glass ionomer cement specimens, and then grinding the hardened glass ionomer specimens into fine powders. All the traditional glass ionomers, resin-modified glass ionomers, and compomers available, and many under development, can be used to be ground into powders. All the usual grinding or milling techniques can be used to grind the pre-cured material into powders. The ground particle size can range from 0.1 $\mu$m to 500 $\mu$m, preferably from 0.5 to 50 $\mu$m. All the dental resin monomers available, and many under development, can be used.

Another embodiment would be to fill dental resins with a mixture of whiskers, reactive ion-releasing fluorosilicate glass powders, and polyacid powders. In this technology, the whiskers are mixed with reactive ion-releasing fluorosilicate glass powders and polyacid powders. The mixture is then silanized and blended with dental resin monomers and cured. The "whiskers" can be silicon-containing whiskers or chopped fibers, or whisker-silicate filler mixtures, or silicate particle-coated whiskers. All the whiskers and chopped fibers available, and many under development, can be used. All types of reactive ion-releasing fluorosilicate glass available, and many under development, can be used. All types of powdered polyacid currently used in dental glass ionomers, and many under development, can be used. All the dental resin monomers available, and many under development, can be used.

Both direct compomer restorations and indirect dental compomers reinforced with whiskers (e.g., inlays, onlays, crowns, and bridges) can be fabricated by using the same procedures for whisker surface treatments, whisker-silicate or fluorosilicate particle mixing and/or bonding, and whisker-glass-polyacid mixing and/or silanization.

Both single layer or laminated whisker-reinforced compomer restorations can be fabricated. Due to the possible refractive index mismatches between fillers and matrices, a single whisker-reinforced compomer or glass ionomer restoration may be opaque. To improve the aesthetic appearance of the restoration, an aesthetic layer can be coated on top of the whisker-reinforced restoration. The outer layer can also prevent direct contact of whiskers with opposing enamel preventing possible excessive wear of enamel. The outer layer can be, but is not limited to, a conventional compomer, a resin-modified glass ionomer, or a dental composite resin.

The present invention will be further understood in view of the following examples which are merely illustrative and not meant to limit the scope of the invention.

III. Preparation of Whisker Reinforced Composite Resins

A dental resin monomer, containing Bis-GMA and TEGDMA at a 1:1 weight ratio, is divided into two equal parts. Part I is mixed with a weight fraction of 0.05% BHT and 2% benzyl peroxide, designated as monomer I. Part II is mixed with 1% of dihydroxy ethyl-P-toluidine (monomer II). Equal weight fraction of fillers (whiskers, whisker glass mixtures, etc.) are then mixed with monomers I and II to form pastes I and II, respectively. The two pastes are then mixed thoroughly and filled into a rectangular cavity of a dimension of 2 mm×2 mm×25 mm in a steel mold to make flexural specimens. Each specimen is incubated at 37° C. for 10 min to chemically cure and then taken out of the mold. The specimens are subsequently immersed in water at 37° C. for 24 h before testing.

EXAMPLE 1

The following whisker reinforced dental composite resins are fabricated:

1. The as-received silicon nitride whiskers are directly silanized. Dental resin composite specimens are then fabricated using the above procedures. This composite material is designated as SNW.
2. The as-received whiskers are heat-treated in air at 500° C. for 30 min to form a surface silicon dioxide layer and then silanized and used. This dental composite is designated as SNWh.
3. The heat-treated (500° C., 30 min) whiskers are mixed with a microfill glass (fumed silicate) at a whisker: glass weight ratio of 2:1, then silanized and used. This composite is designated as SNWg.
4. The as-received silicon nitride whiskers are mixed with a microfill glass (fumed silicate) at a whisker: glass weight ratio of 2:1. The mixture is then heat-treated at 800° C. for 30 min to fuse the glass particles onto the whisker surfaces. The fused whisker-glass mixture is then silanized and used. This composite thus made is designated as SNWfg.

As a control, two conventional dental composites, one reinforced with a microfill glass (fumed silicate) and the other with a macrofill glass (barium oxide), are fabricated and tested in the same manner as the whisker reinforced composites.

Examples of the results from mechanical testing are listed in Table 1. These results were obtained by a standard three-point flexural test. Other standard tests that have also been performed include diametral tensile strength (DTS), compressive strength, micro hardness, and fracture toughness using precracked specimens. The mechanical properties of SNWfg were significantly ($p<0.05$, ANOVA) improved over those of conventional microfill and macrofill composites. For example, the flexural strength value is increased by more than 70%, and the work-of-fracture (i.e., the energy required to fracture the specimen; an indication of toughness) is increased by 100%.

TABLE 1

Mechanical properties of dental composite resins

| Dental composite resin materials | Filler Level wt % | Flexural Strength MPa ± sd (n = 6) | Work-of-Fracture (kJ/m$^2$) | Young's Modulus (GPa) |
|---|---|---|---|---|
| Conventional microfill dental composite resin | 50 | 83 ± 14 | 1.9 ± 0.6 | 2.4 ± 0.3 |
| Conventional macrofill dental composite resin | 78 | 109 ± 13 | 1.4 ± 0.3 | 5.6 ± 0.6 |
| Whisker-reinforced, SNW | 50 | 90 ± 10 | 0.9 ± 0.02 | 5.5 ± 1.3 |
| Whisker-reinforced, SNWh | 43 | 133 ± 5 | 2.4 ± 0.4 | 5.1 ± 0.6 |
| Whisker-reinforced, SNWg | 53 | 158 ± 13 | 2.7 ± 0.5 | 6.1 ± 0.7 |
| Whisker-reinforced, SNWfg | 57 | 195 ± 8 | 3.9 ± 0.5 | 7.1 ± 0.5 |

EXAMPLE 2

Effect of Whisker Oxidation

Using the above procedures, four whisker-reinforced composites were fabricated. The first composite was reinforced with the as-received silicon nitride whiskers silanized. In the other three composites, the whiskers were heat-treated at temperatures of 300° C., 500° C. and 800° C., respectively, for 30 min to form a surface $SiO_2$ layer, then silanized and mixed with resin to make specimens.

TABLE 2

Flexural strength of dental composites vs. whisker oxidation heat-treatment

| Material | Filler weight fraction (wt %) | Flexural strength MPa ± sd (n = 6) |
|---|---|---|
| Conventional microfill dental composite (fumed silicate) | 50 | 83 ± 14 |
| Conventional a microfill dental composite (barium silicate) | 78 | 109 ± 13 |
| Amalgam | Dispersalloy | 86 ± 20 |
| Whisker composite (whisker were silanized) | 50 | 90 ± 10 |
| Whisker composite (whiskers were heat-treated in air at 300° C. to form surface $SiO_2$, and then silanized) | 45 | 117 ± 8 |
| Whisker composite (whisker: 500° C., then silanized) | 43 | 133 ± 5 |
| Whisker composite (whisker: 800 ° C., then silanized) | 43 | 122 ± 8 |

Table 2 shows that the whisker heat-treatment increased the composite strength, with the highest strength ($p<0.05$; ANOVA) at a temperature of 500° C. The filler level was different for different composites in order to achieve a similar working viscosity for the resin pastes. The strength of the whisker composite (500° C.) at a filler weight fraction of 43% was 1.22 times of the strength of the conventional macrofill composite at a filler fraction of 78%.

EXAMPLE 3

Whisker-Glass Mixing and the Effect of Whisker/Glass Ratio

Dental glass particles were mixed with the silicon nitride whiskers to separate the whiskers preventing entanglement, and to improve the packing and increase the filler level. The silicon nitride whiskers were heat treated at 500° C. for 30 min to form surface $SiO_2$, and then mixed with the microfill glass at three whisker/[whisker+glass] weight fractions; 33%, 50% and 67%. Mixing was done in copious ethyl alcohol in a glass beaker with magnetic bar stirring on a hot plate to dry. The dried mixture was silanized and used to reinforce a dental resin. The results are listed in Table 3.

TABLE 3

Effect of whisker weight fraction on strength of composites

| Material | Total filler level (wt %) | Flexural strength MPa ± sd (n = 6) |
|---|---|---|
| Whisker composite (w/wg* = 33%) | 51 | 131 ± 18 |
| Whisker composite (w/wg = 50%) | 58 | 131 ± 17 |
| Whisker composite (w/wg = 67%) | 53 | 158 ± 13 |

*w/wg = whisker/[whisker + glass filler] weight fraction.

Table 3 shows that at a whisker weight fraction of 67%, the composite had a significantly larger strength ($p<0.05$; ANOVA) than the other composites (including those in Table 2). The total filler level was different in order to achieve a similar working viscosity for different resin pastes.

EXAMPLE 4

High Temperature Fusion of Dental Glass Particles onto the Whiskers

Instead of simply mixing whiskers with dental glass particles, the glass particles were fused onto the surfaces of the individual whiskers. The fusion was achieved by first mixing the whiskers with fumed silicate glass particles, at a whisker/[whisker+glass] weight fraction of 67%, in ethyl alcohol with magnetic bar stirring on a hot plate to dry. The dried powders were heat-treated at elevated temperatures to fuse the glass particles onto the whisker surfaces. Four temperatures were used: 650° C., 800° C., 900° C. and 1000° C. The glass-fused whiskers were then silanized and used to fabricate resin composites. The results are listed in Table 4.

TABLE 4

Effect of fusion temperature on glass particle-fused whisker composites

| Material | Total filler level (wt %) | Flexural strength MPa ± sd (n = 6) |
|---|---|---|
| Glass particle-fused whisker (650° C.) composite | 53 | 158 ± 19 |
| Glass particle-fused whisker (800° C.) composite | 57 | 195 ± 8 |
| Glass particle-fused whisker (900° C.) composite | 53 | 182 ± 33 |
| Glass particle-fused whisker (1000° C.) composite | 53 | 139 ± 17 |

Table 5 shows that fusing glass particles onto the whiskers at 800° C. significantly ($p<0.05$; ANOVA) increases the strength of the composite resin compared to the un-fused glass-whisker mixtures (Table 3).

EXAMPLE 5

Mechanical Properties

Young's modulus (i.e., material's resistance to elastic deformation) and work-of-fracture (energy needed to fracture a specimen) of the composites were measured in three-point flexural test. The fracture toughness (i.e., material's resistance to crack propagation) was measured using a single-edged notched test (ASTM Standards E399, 1983) with notched specimens fabricated in a steel mold with a razor blade insert to produce a sharp notch. The results are listed in Table 5.

TABLE 5

Mechanical properties of dental materials

| Material | Flexural strength (MPa) | Young's modulus (GPa) | Work-of-fracture (kJ/mm$^2$) | Fracture toughness MPa.m$^{1/2}$) |
|---|---|---|---|---|
| Conventional microfill dental composite (filler level 57 wt %) | 83 ± 14 | 2.4 ± 3 | 1.9 ± 0.6 | 0.9 ± 0.2 |
| Conventional macrofill dental composite (filler level 78 wt %) | 109 ± 13 | 5.6 ± 0.6 | 1.4 ± 0.3 | 1.3 ± 0.1 |
| Amalgam (Dispersalloy) | 86 ± 20 | 27 ± 3 | 0.2 ± 0.1 | 1.0 ± 0.1 |
| Whisker composite resin* (filler level 57 wt %) | 195 ± 8 | 7.1 ± 0.5 | 3.9 ± 0.5 | 2.3 ± 0.2 |

*Silicon nitride whiskers were fused with microfill glass particles at whisker/[whisker + glass] = 67 wt %.

EXAMPLE 6

Indentation Response

Figure 3A:
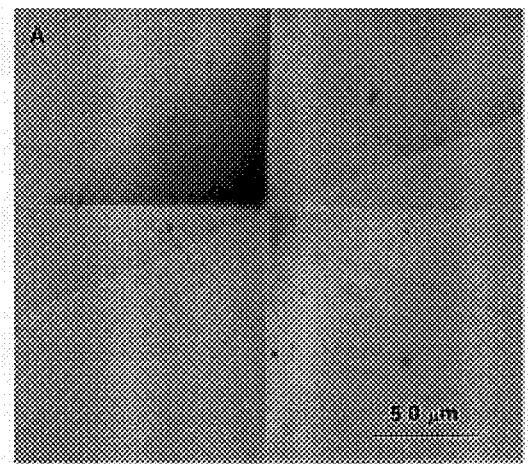
FIG. 3 is Vickers indentation at 10N in (a) conventional microfill, (b) conventional macrofill, and (c) whisker-reinforced dental composite resins. Note the large impression in the microfill hence a small hardness value, and the indentation-induced cracks in the macrofill. The new whisker-reinforced composite resin, while as hard as the macrofill, is free of any cracks, as confirmed by high magnification SEM, suggesting a high resistance to contact damage and wear.
Figure 3B:
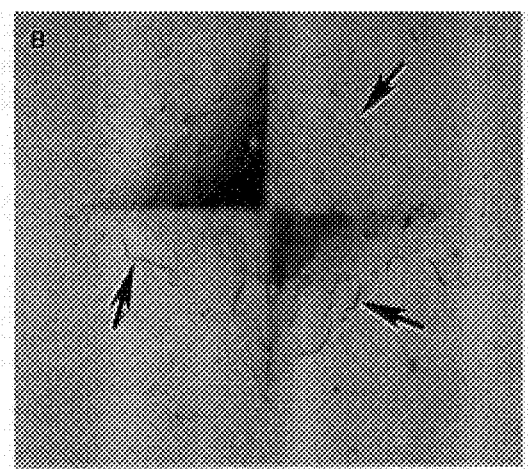
Figure 3C:
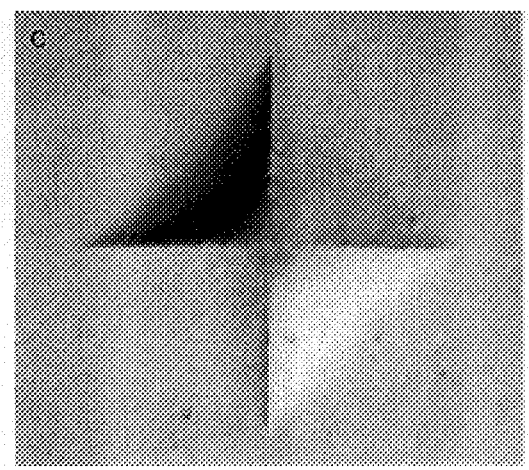

Indentation testing was performed to evaluate the contact and wear response of the composites. A material susceptible to contact damage and wear usually shows one or both of the following indentation responses: a large indentation impression due to the softness of the material, and micro-cracking due to the brittleness of the material (Xu et al., 1995, *J Mater Res* 10, 3204: 3209; 1995, *J Am Ceram Soc,* 78: 497–500). In other words, high wear resistance requires high values of hardness and toughness. Selected composites fabricated in this invention were indented using a Vickers diamond pyramid at a load of 10N to produce six indentations in each material. Optical micrographs of a typical indentation impression is shown in FIGS. 3a–c for (a) conventional microfill dental composite, (b) conventional macrofill, and (c) whisker reinforced dental composite. The microfill composite showed a big impressions, hence a small hardness value. The macrofill is harder; however, numerous indentation-induced micro-cracks are present (arrows in FIG. 3b). On the other hand, the whisker-reinforced composite, (c), while as hard as the macrofill, showed no cracks around and within the indentation impressions, as verified by high magnification scanning electron microscopy (SEM) examination.

IV. Preparation of Compomers and Resin-modified Glass Ionomers

Data on three material systems are provided here as illustrations: (1) ceramic whiskers or chopped fibers are used to reinforce conventional dental compomers or resin-modified glass ionomers that contain reactive ion-releasing fluorosilicate glass fillers; (2) whiskers or fibers are mixed with ground pre-cured glass ionomer powders, silanized, and then incorporated into dental resins; (3) whiskers or fibers are blended with un-cured reactive ion-releasing fluorosilicate glass particles and powdered polyacid; the mixture is silanized and then incorporated into dental resins. (2) and (3) differ from (1) in that no carboxylic acid monomer is used, and all the fillers are silanized. (2) differs from (3) in that pre-cured glass ionomer powders are used in (2), while un-cured reactive fluor-glass and polyacid powders are used in (3). In all cases in this invention, dental silicate filler particles are coated onto the individual whiskers or chopped fibers, to improve the efficacy of whisker silanization, avoid whisker entanglement, and improve the retention of whiskers in matrix by providing rougher whisker surfaces.

EXAMPLE 7

Ceramic Whisker Reinforcement of Conventional Compomers

In this technology, ceramic whiskers are incorporated into currently used dental compomers without reducing their content of reactive ion-releasing fluorosilicate glass and acidic monomers.

In the whisker-reinforced compomers fabricated in this invention, the filler powder was a mixture of two parts: (1) a reactive fluoride-releasing Sr-glass; and (2) ceramic whiskers.

Silicon carbide single-crystalline whiskers were mixed with a commercial microfill dental glass (0.04 μm particle size) at a whisker to glass weight ratio of 3:1. The mixture was then heat-treated at 800° C. to fuse the glass particles onto the individual whiskers. The glass-fused whiskers were silanized by mixing with 3-methacryloxypropyltrimethoxysilane (MPTMS). The silanized whiskers were then mixed with the reactive fluoride-releasing Sr-glass at a weight ratio of 4:1.

Chemical curing was performed to make the compomer specimens. A dental resin monomer, containing Bis-GMA and TEGDMA at a 1:1 weight ratio, was divided into two equal parts. Part I was mixed with a weight fraction of 0.05% BHT and 2% benzoyl peroxide, designated as resin monomer I. Part II was mixed with 1% of dihydroxyethyl-P-toluidine (resin monomer II). Each resin monomer was then mixed with the carboxylic acid monomer (methacryloyloxyethyl phthalate, or MEP), at a resin/MEP weight ratio of 4:1. Equal weight fraction of fillers (containing reactive fluoride-releasing Sr-glass and whiskers) were then blended with the two liquids to form pastes I and II, respectively. The two pastes were then mixed thoroughly and filled into a steel mold of dimension 2 mm×2 mm×25 mm to make flexural specimens.

As controls, two conventional compomers were fabricated using the same resin/MEP ratio as above. One control compomer contained a mixture of silanized microfill glass and reactive fluoride-releasing Sr-glass at 4:1 ratio; the other a mixture of a silanized hybrid filler glass and Sr-glass at 4:1 ratio. Therefore, the contents of reactive fluoride-releasing Sr-glass and acidic monomer were kept the same in the control compomers and in the whisker-reinforced compomers.

Two specimen treatments were performed: (1) specimens were kept dry at 37° C. for 24 hours prior to testing; and (2) specimens were immersed in distilled water at 37° C. for 24 hours prior to testing. The specimens were fractured by using a standard three-point flexural test (ASTM F417–78, 1984) to obtain flexural strength (equal to the applied stress required to fracture the specimen) and work-of-fracture (energy required to fracture the specimen; an indication of fracture toughness). The results are listed in Table 6.

Flexural strength and work-of-fracture values of the whisker-reinforced compomers are significantly larger ($p<0.05$; ANOVA) than those of the controls. Ceramic whisker reinforcement of compomers has increased the flexural strength by 36%–87%, and work-of-fracture by 55%–186%. For comparison, the flexural strength values for dental amalgam are 110–150 MPa and for composite resins are 100–145 MPa (Hickel, *Acad Dent Mater Trans* 9: 105, 1996).

TABLE 6

Mechanical properties of whisker-reinforced and control compomers

| Material | Flexural strength MPa ± sd (n = 8) | Work-of-fracture kJ/mm$^2$ ± sd |
|---|---|---|
| Silicon carbide whisker-reinforced compomer, dry | 148 ± 17 | 1.57 ± 0.26 |
| Silicon carbide whisker-reinforced compomer, wet | 148 ± 14 | 1.89 ± 0.27 |
| Control 1: compomer with microfill glass, dry | 82 ± 22 | 0.79 ± 0.30 |
| Control 1: compomer with microfill glass, wet | 97 ± 17 | 1.22 ± 0.54 |
| Control 2: compomer with hybrid glass, dry | 109 ± 10 | 0.83 ± 0.21 |
| Control 2: compomer with hybrid glass, wet | 79 ± 18 | 0.66 ± 0.20 |

EXAMPLE 8

New Compomers: Resins Filled with Ceramic Whiskers and Pre-Cured Glass Ionomers

As an example of the new compomer technology, pre-cured glass ionomer specimens were ground into powders, mixed with ceramic whiskers, silanized, and then used to reinforce a dental resin. The fabrication procedures are briefly outlined in the following.

The filler powder consisted of a mixture of two parts: (1) ground pre-cured glass ionomer particles; and (2) ceramic whiskers. The powders (1) and (2) are described in the following.

(1) The ground pre-cured glass ionomer particles were obtained by grinding cured glass ionomer specimens into powders. The glass ionomer specimens were fabricated by mixing a blended powder of a commercial reactive ion-releasing fluorosilicate glass and polyacid with distilled water. The powder to liquid weight ratio was 5:1. The mixed paste was filled into a steel mold with a cavity of 2 mm×2 mm×20 mm and hardened at 37° C. for 24 hours. The hardened glass ionomer specimens were then ground into powders by mortar and pestle.

(2) The ceramic whiskers were mixed with a commercial microfill dental glass at a whisker to glass weight ratio of 3:1. The mixture was then heat-treated at 800° C. to fuse the glass particles onto the individual whiskers. Two types of single-crystalline ceramic whiskers were used: silicon nitride, and silicon carbide.

The two powders (1) and (2) were then mixed. The mixed powder was silanized by mixing with 3-methacryloxypropyltrimethoxysilane (MPTMS) in cyclohexane containing n-propylamine as a catalyst.

Chemical curing was performed to make the resin specimens. A dental resin monomer, containing Bis-GMA and TEGDMA at a 1:1 weight ratio, was divided into two equal parts. Part I was mixed with a weight fraction of 0.05% BHT and 2% benzoyl peroxide, designated as monomer I. Part II was mixed with 1% of dihydroxyethyl-P-toluidine (monomer II). Equal weight fraction of fillers (containing ground glass ionomer particles and ceramic whiskers) were then mixed with monomers I and II to form pastes I and II, respectively. The two pastes were then mixed thoroughly and filled into a steel mold with a dimension of 2 mm×2 mm ×25 mm. Each specimen was incubated at 37° C. for 24 hours and then demolded.

The specimens were fractured by using a standard three-point flexural test (ASTM F417–78, 1984) to obtain flexural strength (equal to the applied stress required to fracture the specimen) and work-of-fracture (energy required to fracture the specimen; an indication of fracture toughness). The results are listed in Table 7.

The new compomers containing ground glass ionomer powders and ceramic whiskers, developed in this invention, have flexural strength and work-of-fracture values approximately 3 times of those of glass ionomer specimens from which the pre-cured glass ionomer powders were obtained, and of those of a resin-modified glass ionomer. For comparison, the flexural strength values for dental amalgam are 110–150 MPa and for composite resins are 100–145 MPa (Hickel, *Acad Dent Mater Trans* 9: 105, 1996).

TABLE 7

Mechanical properties of new compomers filled with ground pre-cured glass ionomer powder and whiskers

| Material | Flexural strength MPa ± sd (n = 8) | Work-of-fracture kJ/mm$^2$ ± sd |
|---|---|---|
| New compomer filled with pre-cured glass ionomer powder and SiC whiskers, whisker/glass ionomer = 4:1 | 160 ± 15 | 1.87 ± 0.30 |
| New compomer filled with pre-cured glass ionomer powder and SiC whiskers, whisker/glass ionomer = 2:1 | 140 ± 11 | 1.58 ± 0.27 |
| New compomer filled with pre-cured glass ionomer powder and Si$_3$N$_4$ whiskers, whisker/glass ionomer = 2:1 | 150 ± 10 | 1.63 ± 0.28 |
| Glass ionomer (Ketac) | 38 ± 12 | 0.10 ± 0.06 |
| Glass ionomer (ChemFil II) | 16 ± 2 | 0.15 ± 0.01 |
| Resin-modified glass ionomer (3M) | 48 ± 24 | 0.52 ± 0.32 |

EXAMPLE 9

New Compomers: Resins Containing Reactive Fluor-Glass, Polyacid, and Whiskers

As an example of the new compomer technology, a mixture of reactive ion-releasing fluorosilicate glass particles and powdered polyacid was silanized and blended with dental resins. Two different filler powders were prepared:

(i) This filler powder consisted of a mixture of three parts: (1) reactive ion-releasing fluorosilicate glass particles; (2) powdered polyacid; and (3) ceramic whiskers. A commercial glass ionomer powder, which is a mixture of reactive ion-releasing fluorosilicate glass and powdered polyacid, was used. Ceramic single-crystalline whiskers (e.g., silicon nitride, silicon carbide) were mixed with a commercial microfill dental glass at a whisker to glass weight ratio of 3:1. The mixture was then heat-treated at 800° C. to fuse the glass particles onto the individual whiskers. The glass particle-fused whiskers were then mixed with the commercial glass ionomer powder at a weight ratio of 2:1. The powder was then silanized as previously described.

(ii) This filler powder consisted of a mixture of three parts: (1) reactive ion-releasing fluorosilicate glass particles; (2) powdered polyacid; and (3) dental silicate filler particles. No whiskers were used in this case. A commercial microfill glass was used to mix with a commercial glass ionomer powder which is a mixture of reactive ion-releasing fluorosilicate glass particles and powdered polyacid. The ratio of microfill glass to glass ionomer powder was 1:1. The mixture was then silanized as previously described.

Chemical curing was performed to make the resin specimens. A dental resin monomer, containing Bis-GMA and TEGDMA at a 1:1 weight ratio, was divided into two equal parts. Part I was mixed with a weight fraction of 0.05% BHT and 2% benzoyl peroxide, designated as monomer I. Part II was mixed with 1% of dihydroxy ethyl-P-toluidine (monomer II). Equal weight fraction of fillers (containing reactive ion-releasing fluorosilicate glass particles, powdered polyacid, and whiskers or microfill glass) were then mixed with monomers I and II to form pastes I and II, respectively. The two pastes were then mixed thoroughly and filled into a rectangular cavity of a dimension of 2 mm ×2 mm×25 mm in a steel mold. Each specimen was incubated at 37° C. for 24 hours and then demolded.

The specimens were fractured by using a standard three-point flexural test (ASTM F417–78, 1984) to obtain flexural strength (equal to the applied stress required to fracture the specimen) and work-of-fracture (energy required to fracture the specimen; an indication of fracture toughness). The results are listed in Table 8.

The new whisker compomers, which are resin composites filled with reactive ion-releasing fluorosilicate glass, polyacid and whiskers, had significantly larger strength and work-of-fracture values than those of the other materials ($p<0.05$; ANOVA).

TABLE 8

Mechanical properties of new compomers filled with reactive fluorosilicate glass and polyacid

| Material | Flexural strength MPa + sd (n = 8) | Work-of-fracture kJ/mm$^2$ + sd |
|---|---|---|
| New compomer: resin filled with reactive fluoride ion-releasing glass, polyacid, and silicon nitride whiskers | 137 ± 11 | 1.54 ± 0.31 |
| New compomer: resin filled with reactive fluoride ion-releasing glass, polyacid, and silicon carbide whiskers | 126 ± 12 | 1.28 ± 0.19 |
| New compomer: resin filled with reactive fluoride ion-releasing glass, polyacid, and microfill glass, microfill/ionomer = 1:1 | 97 ± 12 | 0.92 ± 0.20 |
| Glass ionomer (Ketac) | 38 ± 12 | 0.10 ± 0.06 |
| Glass ionomer (ChemFil II) | 16 ± 2 | 0.15 ± 0.01 |
| Resin-modified glass ionomer (3M) | 48 ± 24 | 0.52 ± 0.32 |

EXAMPLE 10

Fluoride Release

The cured specimens were immersed in distilled water for 100 hours and the cumulative fluoride release was measured with a fluoride ion selective electrode as usual. The results are listed in Table 9.

The new compomers containing whiskers, while mechanically much stronger and tougher, release significantly more fluoride ($p<0.05$; ANOVA) than the control compomer containing only glass particles.

TABLE 9

Fluoride Release

| Material | 100 hr Accumulative release ($\mu$g/mm$^2$) |
|---|---|
| Ketac traditional glass ionomer control | 128 |
| Traditional glass compomer control | 1.3 |
| Resin composite (dental microfill) control | can't be detected |
| SiC whisker-reinforced compomer | 0.82 |
| New compomer: Si$_3$N$_4$ whisker + Ketac glass and acid powder, 2:1 | 11.5 |
| New compomer: SiC whisker + pre-cured Ketac, 2:1 | 26.9 |
| New compomer: Si$_3$N$_4$ whisker + pre-cured Ketac, 4:1 | 77.6 |

While the primary benefits of the present invention are believed to relate to dental applications, it is also contemplated that the methods and compositions disclosed herein, e.g., the surface silicon dioxide formation of whiskers for silanization, the mixing of whiskers with particle fillers to better disperse the whiskers and chopped fibers from each other to avoid entanglement and to increase filler level by bimodal distribution, and the bonding of filler particles onto the whiskers for improved retention in matrix by providing rougher whisker surfaces, may be employed in conjunction with industrial, medical and veterinary uses, for example, industrial polymeric composites, structural polymeric composites, and bone replacement polymeric composites.

CONCLUSION

The composition of the invention is, as stated above, especially useful as a restorative dental material. Multiple other uses, however, are as discussed, possible and appropriate. The material is a mixture of "whiskers," as defined herein, in a matrix. The term "whiskers" is to be interpreted broadly and includes not only whiskers (which are generally single crystalline, but may also be polycrystalline), but also fibers and other materials of like nature (such as single crystalline, polycrystalline and glassy materials and organic materials) which have a general geometrical configuration wherein the longitudinal dimension thereof exceeds the transverse or diameter dimension in the manner described. In addition, the whiskers in the preferred embodiment are coated with a layer that promotes adhesion of the whiskers in the matrix material. That is, the whiskers are coated with a silicon dioxide containing coating. The silicon dioxide containing coating is effected in any one of numerous ways, including fusing of silicon dioxide containing beads to the whisker, sputtering deposition, chemical reaction coating, oxidation of a silicon-containing whisker by annealing at a high temperature, and by any other means by which an appropriate layer or partial layer of silicon dioxide containing material is provided on the surface of the whisker. This partial layer or full layer of silicon dioxide containing material typically interacts with another material to silanize the whisker. Thus, the whisker has a layer containing $S_iO_2$ thereon and a layer of a silanization material. Further, the matrix composition may include various types of particles, including filler particles. Part of these particles may be bonded to the whisker by virtue of fusing to the silicon dioxide containing beads. The silicon dioxide acts as an agent to enhance such a bonding operation. Importantly, the particles (whether silicon dioxide containing or otherwise) which are bonded to the whiskers act to roughen the surface of the whiskers. The roughened surfaces are silanized and will interact with a polymeric matrix to provide a much stronger composition.

In sum, the silicon dioxide containing layer acts as interface layer not only for the particles when particles are bonded onto the whiskers, but with respect to the chemical used for the silanization coating. The result is a much better interaction and bonding of the whiskers with the polymeric matrix material. As a result, the mechanical properties of the material are greatly enhanced relative to the prior art. Additionally the filler particles may include releasable fluoride. Thus, the silicon dioxide facilitates joining of the particles with the whiskers. The particles may provide for fluoride release which is a desirable aspect of dental restorative materials. Further, the particles tend to roughen the surface of the whiskers thereby enhancing the bonding effect of the whiskers with the polymeric matrix.

Thus while specific examples of the invention have been set forth, variations are within the scope of the invention, and the invention is therefore defined by the following claims and equivalents thereof.

What is claimed is:

1. A composition useful as a restorative material comprising, in combination:
   a) from five percent (5%) by weight to ninety-five percent (95%) by weight of a curable matrix material taken from a group consisting of polymerics, glass ionomers, resin modified glass ionomers, polyacids, plastic resin monomers, water based cements, thermoset resin monomers, and mixtures of two or more of said materials; and
   b) a first dispersed solid material in the matrix of up to ninety-five percent (95%) by weight of precoated whiskers taken from a group consisting of single crystalline ceramic materials, polycrystalline ceramic materials, glass fiber materials, metal fiber materials, polymer fiber materials, and mixtures of two or more of said materials, said whiskers including solid particulates bonded to at least a portion of the surface thereof.

2. The composition of claim 1 wherein the whiskers have a length-to-diameter ratio in the range of about 2 to 1000.

3. The composition of claim 2 wherein the whiskers have a length-to-diameter ratio in the range of about 5 to 100.

4. The composition of claim 1 wherein the silicon containing compound contains silicon dioxide ($SiO_2$).

5. The composition of claim 1 wherein the whiskers comprise silicon containing materials.

6. The composition of claim 5 wherein the whiskers are annealed to at least partially coat the surface thereof with silicon dioxide ($SiO_2$).

7. The composition of claim 6 wherein the temperature range of annealing is 150° C. to 1000° C.

8. The composition of claim 2 wherein the particulate fillers are fused onto the whiskers in the range of 150° C. to 1600° C.

9. The composition of claim 8 wherein the temperature range is 500° C. to 1000° C.

10. The composition of claim 1 wherein the whiskers have an average diameter in the range of about 0.1 $\mu$m to 100 $\mu$m.

11. The composition of claim 1 wherein the whiskers are a material from a group consisting of silicon nitride, silicon carbide, mullite, alumina, zirconia, sapphire, titanium nitride, metal salts, metal oxides and mixtures of two or more of said materials.

12. The composition of claim 1 wherein the whiskers comprise a mixture of single crystalline ceramic whiskers and fibers taken from a group consisting of polycrystalline fibers, glass fiber, metal fibers, organic fiber and mixtures of two or more of said fibers.

13. The composition of claim 1 wherein the fillers are taken from a group consisting of silicate glass, quartz, silicon nitride, silicon carbide, alumina, zirconia, and mixtures of two or more said materials.

14. The composition of claim 1 wherein the whiskers are at least in part silanized on their surface.

15. The composition of claim 14 wherein the silanization compound comprises 3-methacryloxy-propyltrimethoxysilane.

16. The composition of claim 1 formed as a dental restorative.

17. The composite of claim 1 formed as dental core restorative.

18. The composition of claim 1 including a bonded silicon containing compound on the surface of the whiskers, and said silicon compound is a material taken from a group consisting of silicate materials, fluorosilicate materials, silicon containing ceramic materials, and mixtures of said materials.

19. A method for manufacture of a restorative composition comprising the steps of:
   a) preparing solid material whiskers comprised of a material taken from a group consisting of single crystalline ceramic materials, polycrystalline ceramic materials, glass fiber materials, polymer fiber materials and mixtures of at least two of said materials;
   b) bonding said whiskers at least in part with solid material particles of a silicon containing compound prior to combination with a matrix material;
   c) mixing the whiskers having the particle coating with a curable fluid matrix material taken from a group consisting of polymerics, glass ionomers, resin modified glass ionomers, water based cements and mixtures of two or more of said materials; and
   d) curing the matrix material with the whiskers therein to form the restorative material.

20. The method of claim 19 including the further step of adding a solid filler taken from a group consisting of silicate materials, resins, polymeric composites, powdered precured polymers, powdered precured composite resins, powdered precured glass ionomers, powdered precured hybrid materials and mixtures of two or more said materials when mixing the whiskers with the matrix material.

21. The method of claim 19 wherein the whiskers comprise up to ninety-five percent (95%) by weight of said composition.

22. The method of claim 19 wherein the coating step is effected by bonding particles to the whiskers, chemical coating of the whiskers, sputter coating of the whiskers, or annealing the whiskers.

23. The method of claim 19 including the step of bonding in the temperature range of 150° C. to 1600° C.

24. The method of claim 19 wherein the whiskers are generally uniformly dispersed and mixed in the matrix.

25. The method of claim 19 including the step of adding a fluoride releasing filler particle to the mix when combining the whiskers with the matrix material.

26. A product by the process of claim 19.

27. A composition for a restorative material comprising, in combination:
   a) precoated solid whiskers selected from a group consisting of single crystalline ceramic materials, polycrystalline ceramic fiber materials, glass fiber materials, metal fiber materials, polymer fiber materials and mixtures thereof, said whiskers precoated with filler particles bonded to the surface thereof to cause distribution of the whiskers in the restorative material, said filler materials taken from a group consisting of ceramics, glass and polymeric composites; and b) said precoated whiskers dispersed in a curable, hardenable, fluid, polymeric matrix.

28. The composition of claim 27 wherein the whiskers are taken from a group consisting of oxides, carbides, nitrides, and mixtures thereof.

29. The composition of claim 27 wherein the filler particles are taken from a group consisting of silicon oxide containing glasses, mixed glass and ceramic materials and mixtures thereof.

30. The composition of claim 27 wherein the filler particles are taken from a group consisting of leachable polymeric composites, glass ionomers having releasable fluoride and mixtures thereof.

31. The composition of claim 27 as a dental restorative material.

32. The composition of claim 27 wherein the precoated whiskers are coated with a silicon containing compound.

33. A method for manufacture of a restorative composition comprising the steps of:

a) preparing solid material whiskers comprised of a material taken from a group consisting of single crystalline ceramic materials, polycrystalline ceramic materials, glass fiber materials, polymer fiber materials and mixtures of at least two of said materials;

b) coating said whiskers with a silicon containing compound;

c) bonding said coated whiskers, at least in part, with solid particles of a silicon containing compound prior to combination with a fluid matrix material;

d) mixing the whiskers having the bonded particles with a curable fluid matrix material taken from a group consisting of polymerics, glass ionomers, resin modified glass ionomers, water based cements and mixtures of two or more of said materials; and e) curing the matrix material with the whiskers therein to form the restorative material.

* * * * *

UNITED STATES PATENT AND TRADEMARK OFFICE
CERTIFICATE OF CORRECTION

PATENT NO. : 5,861,445
APPLICATION NO. : 08/852900
DATED : January 19, 1999
INVENTOR(S) : Huakan Xu et al.

Page 1 of 1

It is certified that error appears in the above-identified patent and that said Letters Patent is hereby corrected as shown below:

In the Specification

Column 1, Lines 4-7, should read:
STATEMENT OF FEDERALLY SPONSORED RESEARCH
This invention was made with government support under grants DE009322 awarded by the National Institutes of Health. The government has certain rights in the invention.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*